United States Patent
Petersen

(10) Patent No.: US 10,688,299 B2
(45) Date of Patent: Jun. 23, 2020

(54) ELECTRODE FOR PERIPHERAL NERVE STIMULATION

(71) Applicant: BioVentures, LLC, Little Rock, AR (US)

(72) Inventor: Erika Petersen, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 117 days.

(21) Appl. No.: 15/760,928

(22) PCT Filed: Sep. 19, 2016

(86) PCT No.: PCT/US2016/052488
§ 371 (c)(1),
(2) Date: Mar. 16, 2018

(87) PCT Pub. No.: WO2017/049292
PCT Pub. Date: Mar. 23, 2017

(65) Prior Publication Data
US 2019/0167980 A1    Jun. 6, 2019

Related U.S. Application Data

(60) Provisional application No. 62/220,528, filed on Sep. 18, 2015.

(51) Int. Cl.
*A61N 1/05* (2006.01)
*A61N 1/36* (2006.01)

(52) U.S. Cl.
CPC ......... *A61N 1/0558* (2013.01); *A61N 1/0551* (2013.01); *A61N 1/36075* (2013.01); *A61N 1/0504* (2013.01); *A61N 1/0526* (2013.01)

(58) Field of Classification Search
None
See application file for complete search history.

(56) References Cited

U.S. PATENT DOCUMENTS

| | | | |
|---|---|---|---|
| 7,313,444 B2 * | 12/2007 | Pianca | A61N 1/056 607/126 |
| 8,204,607 B2 | 6/2012 | Rooney et al. | |
| 8,340,779 B2 * | 12/2012 | Harris | A61B 17/3401 607/116 |
| 8,892,214 B2 | 11/2014 | Bonde et al. | |
| 8,892,217 B2 * | 11/2014 | Camps | A61N 1/0587 607/116 |
| 9,220,897 B2 * | 12/2015 | Perryman | A61N 1/36071 |

(Continued)

FOREIGN PATENT DOCUMENTS

| | | |
|---|---|---|
| WO | 2014099423 A1 | 6/2014 |
| WO | 2017049292 A2 | 3/2017 |

OTHER PUBLICATIONS

Abhinav, K. et al., "Novel Use of Narrow Paddle Electrodes for Occipital Nerve Stimulation—Technical Note," Neuromodulation, 2013, pp. 607-609, vol. 16, No. 6.

(Continued)

*Primary Examiner* — Brian T Gedeon
(74) *Attorney, Agent, or Firm* — Polsinelli PC

(57) ABSTRACT

Devices and methods for peripheral nerve stimulation with an electrode assembly having a lead body with a tapered transition, at least one anchor, and at least one distal lead configured to connect to the lead body are disclosed.

19 Claims, 7 Drawing Sheets

(56) References Cited

U.S. PATENT DOCUMENTS

| | | | |
|---|---|---|---|
| 2002/0116042 A1* | 8/2002 | Boling | A61N 1/0531 607/122 |
| 2004/0064172 A1 | 4/2004 | McVenes et al. | |
| 2006/0173259 A1 | 8/2006 | Flaherty et al. | |
| 2008/0039916 A1* | 2/2008 | Colliou | A61N 1/056 607/116 |
| 2008/0103572 A1 | 5/2008 | Gerber | |
| 2008/0132980 A1 | 6/2008 | Gerber | |
| 2010/0274313 A1 | 10/2010 | Boling et al. | |
| 2011/0071606 A1 | 3/2011 | Kast et al. | |
| 2012/0192874 A1 | 8/2012 | Bolea et al. | |
| 2013/0238067 A1 | 9/2013 | Baudino | |
| 2014/0058481 A1 | 2/2014 | Perryman et al. | |
| 2014/0180375 A1 | 6/2014 | Pianca et al. | |
| 2015/0051678 A1 | 2/2015 | Reed et al. | |
| 2015/0165191 A1 | 6/2015 | Frericks et al. | |

OTHER PUBLICATIONS

Al-Jehani, H. et al., "Peripheral Nerve Stimulation for Chronic Neurogenic Pain," Slavin, K. (ed): Peripheral Nerve Stimulation, Prog. Neurol. Surg., Basel, Karger, 2011, pp. 27-40, vol. 24, Abstract Only.

Alo, K. et al., "Percutaneous Peripheral Nerve Stimulation," Slavin, K. (ed): Peripheral Nerve Stimulation, Prog. Neurol. Surg., Basel, Karger, 2011, pp. 41-57, vol. 24, Abstract Only.

Amin, S. et al., "Peripheral nerve stimulator for the treatment of supraorbital neuralgia: a retrospective case series," Cephalalgia, 2008, pp. 355-359, vol. 28, Blackwell Publishing Ltd.

Ducic, I. et al., "A Systematic Review of Peripheral Nerve Interventional Treatments for Chronic Headaches," Ann. Plast. Surg., Apr. 2014, pp. 439-445, vol. 72, No. 4, Lippincott Williams & Wilkins.

Ellens, D. et al., "Peripheral Neuromodulation for Migraine Headache," Prog. Neurol. Surg., 2011, pp. 109-117, vol. 24, S. Karger AG, Basel.

Falowski, S. et al., "Occipital nerve stimulator systems: review of complications and surgical techniques," Neuromodulation, 2010, pp. 121-125, vol. 13.

Franzini, A. et al., "Occipital nerve stimulation (ONS). Surgical technique and prevention of late electrode migration," Acta Neurochir., 2009, pp. 861-865, vol. 151, Springer.

Goadsby, P. et al., "Occipital Nerve Stimulation for Headache: Mechanisms and Efficacy," Headache Currents, Feb. 2008, pp. 313-318, Blackwell Publishing.

International Search Report and Written Opinion dated Mar. 9, 2017 from related PCT Application No. PCT/US2016/052488; 12 pgs.

McRoberts, W. et al., "Peripheral Nerve Field Stimulation for the Management of Localized Chronic Intractable Back Pain: Results From a Randomized Controlled Study," Neuromodulation, 2013, pp. 565-575, vol. 16, No. 6.

Palmisani, S. et al., "A six year retrospective review of occipital nerve stimulation practice—controversies and challenges of an emerging technique for treating refractory headache syndromes," J. Headache Pain, 2013, pp. 1-10, vol. 14, No. 67.

"Peripheral Nerve Stimulation for Intractable Chronic Migraine Fact Sheet," St. Jude Medical, Inc., 2010, 3 pgs., accessible at http://tinyurl.com/qdkb7v2.

Verrills, P. et al., "Peripheral Nerve Field Stimulation for Chronic Headache: 60 Cases and Long-Term Follow-Up," Neuromodulation, Jan. 2014, pp. 54-59, vol. 17, No. 1.

\* cited by examiner

ELECTRODE FOR PERIPHERAL NERVE STIMULATION

CROSS REFERENCE TO RELATED APPLICATION

This application is a US national phase application of PCT application No. PCT/US2016/052488 filed on Sep. 19, 2016, which claims benefit to U.S. Provisional Patent Application No. 62/220,528, filed on Sep. 18, 2015, which is are herein incorporated by reference in their entirety.

FIELD OF THE INVENTION

The disclosure is directed to devices and methods for securing implantable electrodes in a subcutaneous location proximate to a peripheral nerve. In particular, this disclosure is directed to tapered and flexible electrode lead that has a peel away sheath introducer.

BACKGROUND OF THE INVENTION

The peripheral nervous system comprises the nerves and ganglia that are outside of the central nervous system. The central nervous system, which consists of the brain and spinal cord is connected to the limbs and organs by the peripheral nerves. In general the peripheral nervous system controls both sensory and motor functions.

Because the peripheral nervous system is responsible for processing sensory events, the peripheral nerves are also responsible for processing pain. The peripheral nervous system processes pain associated with syndromes such as scalp pain, extremity pain, migraine, and occipital neuralgia. The peripheral nervous system is also responsible for motor functions. These motor functions include movement of extremities and core.

The nerves of the peripheral nervous system provide a pathway for electrochemical nerve impulses. Impairment of these electrochemical pathways may result in an inability to properly process pain resulting in pain such as scalp pain, extremity pain, migraine, and occipital neuralgia. Impairment of peripheral nerves may also result in impairment of a person's motor abilities.

Neuromodulation has been used to alter the nerve activity through the delivery of electrical stimulation or chemical agents. In neuromodulation, electrical stimulation of peripheral nerves is used for modulating firing patterns of neurons. This electrical stimulation can be accomplished by subcutaneous placement of electrodes proximate to a peripheral nerve. The implantable electrodes currently used for neuromodulation are designed for epidural use. Because epidural electrodes, being used off-label, are not designed for neuromodulation in a subcutaneous location there are several complications including infection, skin erosion, pain and electrode fracture.

Existing and currently used epidural electrodes are all one caliber from distal to proximal ends. This single caliber design means that an electrode that is thin enough to be of lower risk for erosion in the subcutaneous location and lower profile is too fragile when traversing the course to the implanted generator site.

Additional shortcomings of existing electrodes include separate anchor systems that require extra steps for implantation and also introduced movement of the electrode which can affect technical performance.

The frailty and mobility of current electrodes may be overcome by using an electrode that is designed to be used specifically for subcutaneous placement over a peripheral nerve. Such an electrode would have a tapered and thin distal electrode in combination with a more robust, wider diameter lead body that is better able to resist the stresses of high motion areas, especially the range of motion in the neck.

A need exists in the art for devices, systems, and methods for an implantable electrode lead designed for neuromodulation applications requiring subcutaneous placement.

DESCRIPTION OF THE FIGURES

The following figures illustrate various aspects of the disclosure.

While multiple embodiments are disclosed, still other embodiments of the present disclosure will become apparent to those skilled in the art from the following detailed description, which shows and describes illustrative embodiments of the disclosure. As will be realized, the disclosure is capable of modifications in various aspects, all without departing from the spirit and scope of the present disclosure. Accordingly, the drawings and detailed description are to be regarded as illustrative in nature and not restrictive.

DETAILED DESCRIPTION

Provided herein is a subcutaneous electrode assembly with a tapered design with a thinner distal lead that provides for a slim profile when implanted under a thin skin layer over a targeted peripheral nerve and a thicker lead body that has resilience to address movement that could otherwise increase fracture or migration risk.

Figure 1:
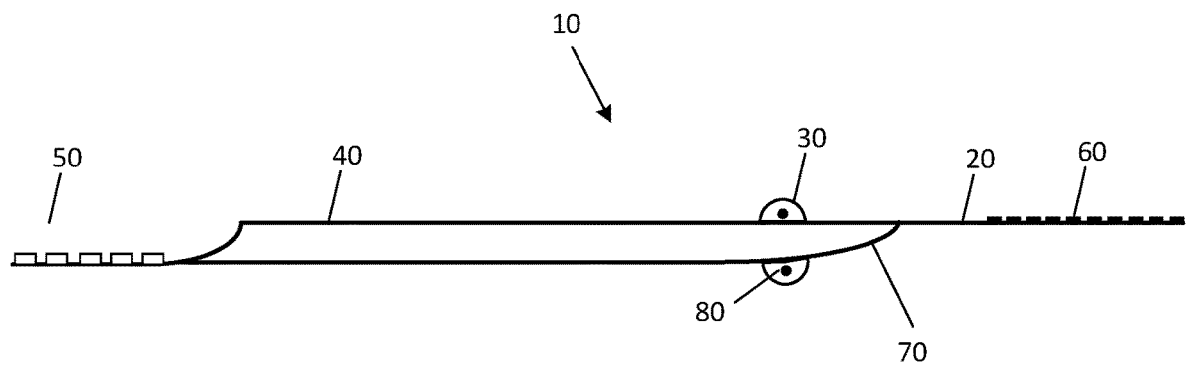
FIG. 1 is a first embodiment of the assembly.
Figure 2:
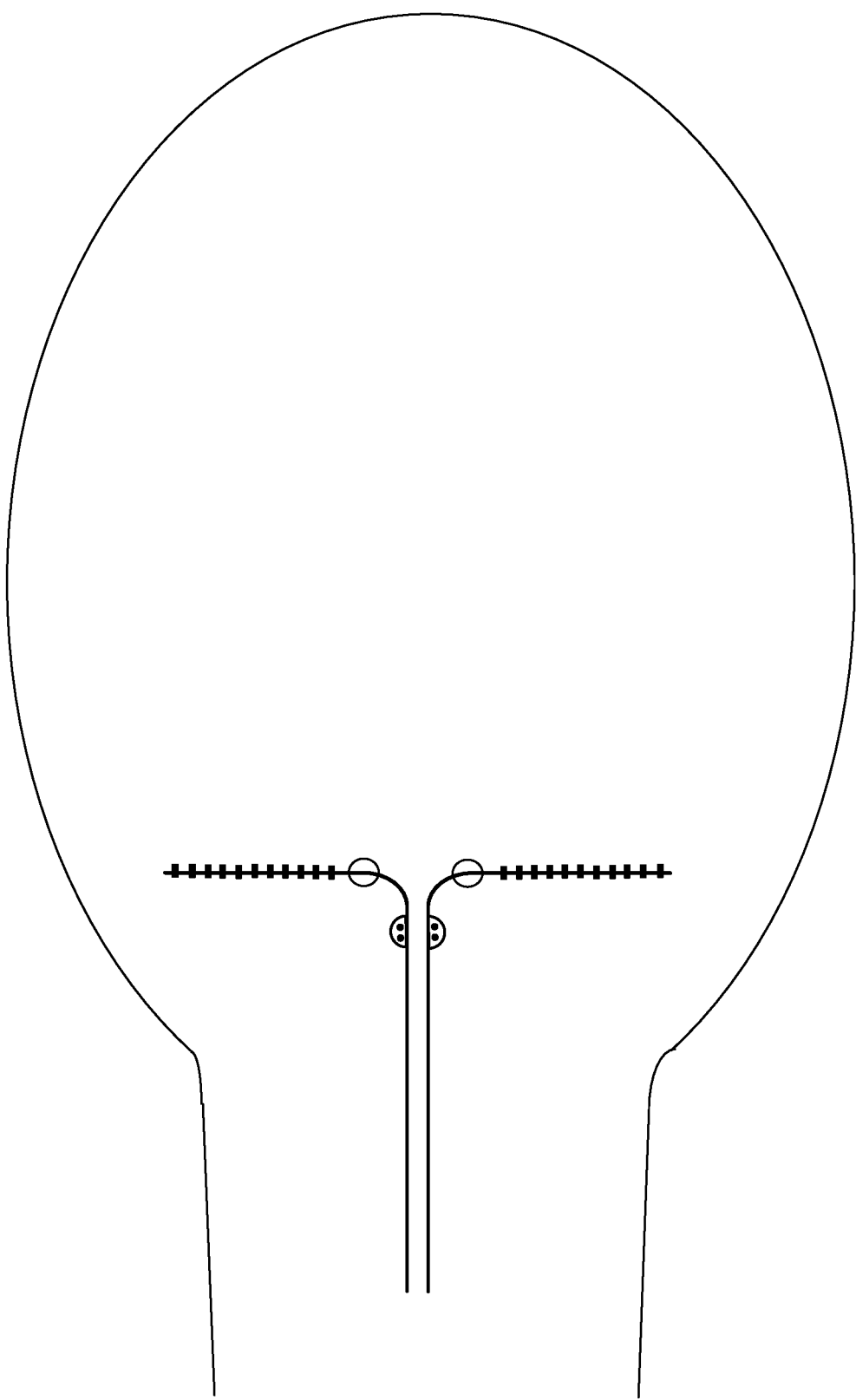
FIG. 2 is a bilateral occipital nerve stimulator in a subject's head.

With reference to FIG. 1, the assembly 10 of the present invention generally comprises one or more distal leads 20, one or more integrated anchors 30, a lead body 40 and a connector element 50. The integrated anchors are proximate to a tapered transition 70. Each distal lead has an array of electrical contacts 60. In preferred embodiments, the distal leads 20, one or more integrated anchors 30, a lead body 40 and a connector element 50 are a unitary body.

The assembly has a first end where the connector element 50 is located. Distal leads 20 are at an end that is opposite of connector element 50. The lead body 40 is located at a point between the connector element 50 and the proximal end of the distal leads 20. In preferred embodiments, the lead body 40 is tapered at one or both ends at a tapered transition 70. The integrated anchors 30 may be located at one or more points on the lead body 40. In a preferred embodiment, the integrated anchors 30 are at the distal end of the lead body 40 proximate to the tapered transition 70. This location of the integrated anchors 30 may secure the assembly such that migration is minimized and anchor-related injury to the lead itself is minimized. The assembly may further include a peel-away introducer. In a non-limiting example, the assembly 10 may be implanted into a subject at a location that is proximate to or touching a peripheral nerve. In additional aspects, a method of implanting the assembly 10 into a subject is provided. The devices, systems, and methods are described in additional detail herein below.

I. Distal Leads

Figure 5:
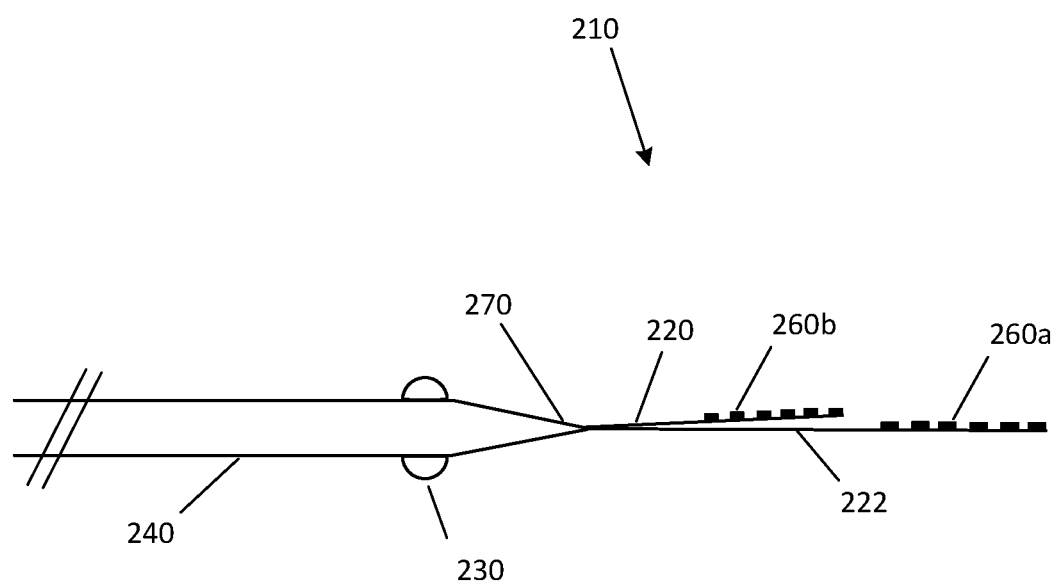
FIG. 5 is an alternate embodiment of the assembly.
Figure 6:
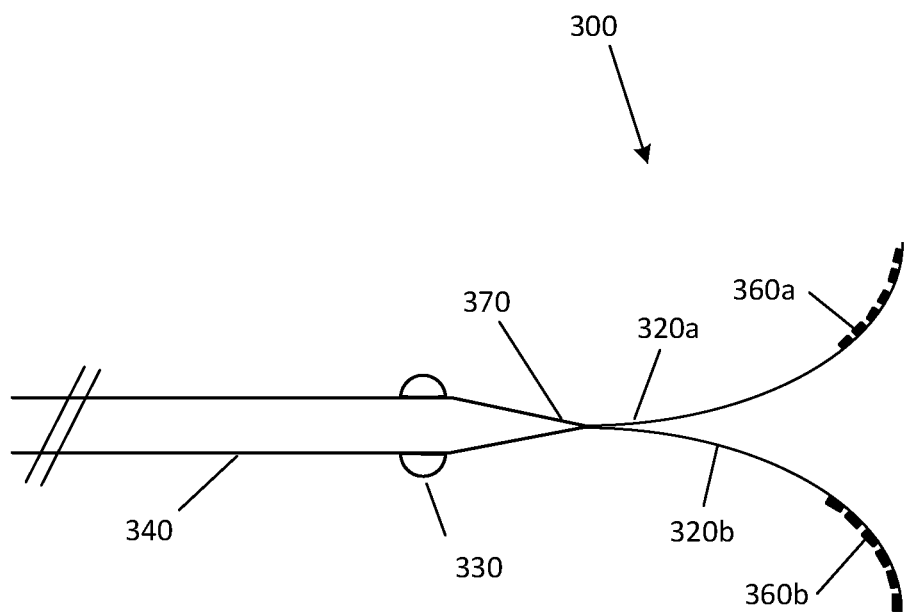
FIG. 6 is an alternate embodiment of the assembly.

The flexible distal leads 20 may be inserted subcutaneously and be in mobile areas. With reference to FIGS. 1 and 4-7, the assembly 10 may comprise any number of distal leads 20 having electrical contacts 60. In one embodiment, the assembly 10 may comprise a single distal lead 20 that is sufficient for holding the electrical contacts. In another embodiment, the assembly may comprise two distal leads as illustrated in FIGS. 5-6. The assembly may comprise any number of distal leads 20. In a non-limiting example, the assembly may comprise 1, 2, 3, 4, 5, 6, 7, 8, 9, or 10 distal leads 20.

In embodiments having a plurality of distal leads 220 and 222, the distal leads 220 and 222 may have different lengths, as illustrated in FIG. 5. In another embodiment with a plurality of distal leads 320, the distal leads 320a and 320b may be of the same length, as illustrated in FIG. 6.

Figure 7:
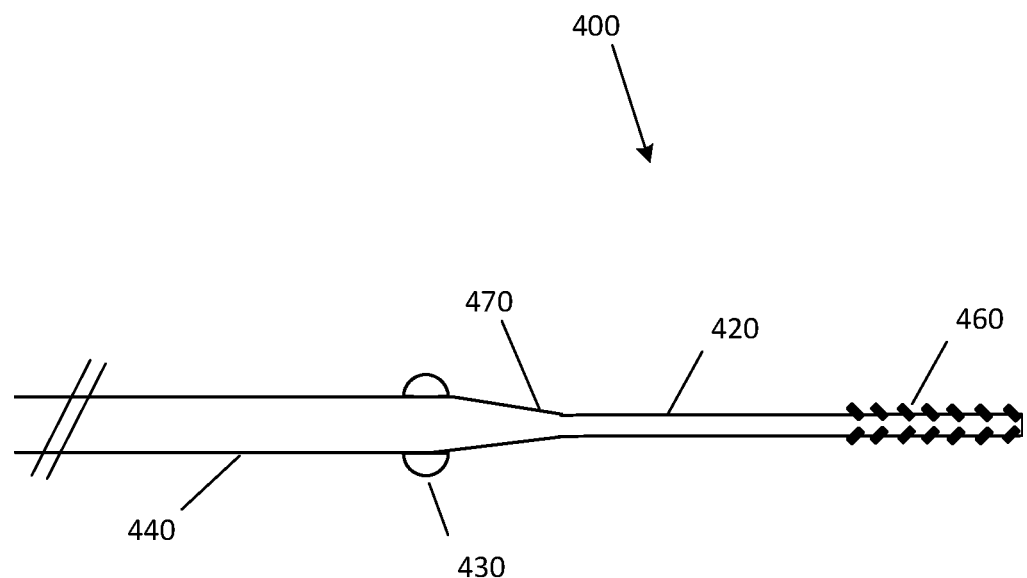
FIG. 7 is an alternate embodiment of the assembly.

In a preferred embodiment, the one or more distal leads have a cylindrical shape. In another embodiment, the one or more distal leads 460 may have a paddle shape as illustrated in FIG. 7. Other possible shapes of the distal lead may be, in a non-limiting example, rectangular, hexagonal, or any three-dimensional shape.

At a first end of the distal lead 20 is an array of electrical contacts 60. At the opposite end of the distal lead 20, where the distal lead 20 meets the lead body 40, is a tapered transition 70 due to the lead body 40 having greater thickness than the distal lead 20 and the integrated anchors 30. In various embodiments, the distance between the array of electrical contacts 60 and the tapered transition 70 may be chosen according to the location that the assembly 10 is to be implanted. In a non-limiting example, the distance between the array of electrical contacts 60 to the tapered transition 70 may be short for occipital nerve stimulation or for implanting in extremities. For example, the distance between the array of electrical contacts 60 and the integrated anchor 30 may range from about 10 mm to about 70 mm. In various aspects, the distance may range from about 10 mm to about 30 mm, from about 20 mm to about 40 mm, from about 30 mm to about 50 mm, from about 40 mm to about 60 mm, and from about 50 mm to about 70 mm. In some embodiments, the distance between the array of electrical contacts 60 and the tapered transition 70 may have an intermediate length for facial implantation. For example, the distance between the array of electrical contacts 60 and the tapered transition 70 may range from about 70 mm to about 180 mm. In various aspects, the distance may range from about 70 mm to about 90 mm, from about 80 mm to about 100 mm, from about 90 mm to about 110 mm, from about 100 mm to about 120 mm, from about 110 mm to about 130 mm, from about 120 mm to about 140 mm, from about 130 mm to about 150 mm, from about 140 mm to about 160 mm, from about 150 mm to about 170 mm, and from about 160 mm to about 180 mm. In other embodiments the distance between the array of electrical contacts 60 and the integrated anchor 30 may be longer for implantation into longer extremities. For example, the distance between the array of electrical contacts 60 and the tapered transition 70 may range from about 80 mm to about 180 mm. In various aspects, the distance may range from about 80 mm to about 100 mm, from about 90 mm to about 110 mm, from about 100 mm to about 120 mm, from about 110 mm to about 130 mm, from about 120 mm to about 140 mm, from about 130 mm to about 150 mm, from about 140 mm to about 160 mm, from about 150 mm to about 170 mm, and from about 160 mm to about 180 mm. One of skill in the art will appreciate that assembly 10 length may be any length that is appropriate for implantation into a desired site.

The distal leads 20 may have a diameter smaller than the diameter of the lead body 40. In an aspect, the diameter of the distal lead 20 may range from about 1 mm to about 0.3 mm, from about 0.8 mm to about 0.6 mm, from about 0.7 mm to about 0.5 mm, from about 0.6 mm to about 0.4 mm, and from about 0.5 mm to about 0.3 mm. In one aspect, the diameter of the distal leads 20 is 0.8 mm. In another aspect, the distal leads 20 may include a plastic lead tip having a diameter of about 0.5 mm. The distal leads may also include an extension component having a diameter ranging from about 1.5 mm to about 0.5 mm. One of skill in the art may appreciate that the distal leads 20 may have a diameter or thickness that provides for subcutaneous implantation of the distal leads 20 over a peripheral nerve.

Each distal lead 20 has at least one array of electrical contacts 60. Because the electrical contacts are a means of passing current to a subject's peripheral nervous system, the electrical leads are preferably made of a conductive material such as a metal. One of skill in the art would appreciate that the conductive material is not limited to metals, but can be any conductive material known in the art.

In preferred embodiments, the distal leads 20 may have an array of electrical contacts 60. In preferred embodiments, the electrical contacts 60 in the array are evenly spaced on each of the distal leads. In other embodiments, the electrical contacts 60 in the array may be spaced in a random arrangement. In various aspects, the electrical contacts 60 may be parallel, perpendicular, or oriented in any direction relative to the distal lead 20.

Figure 4:
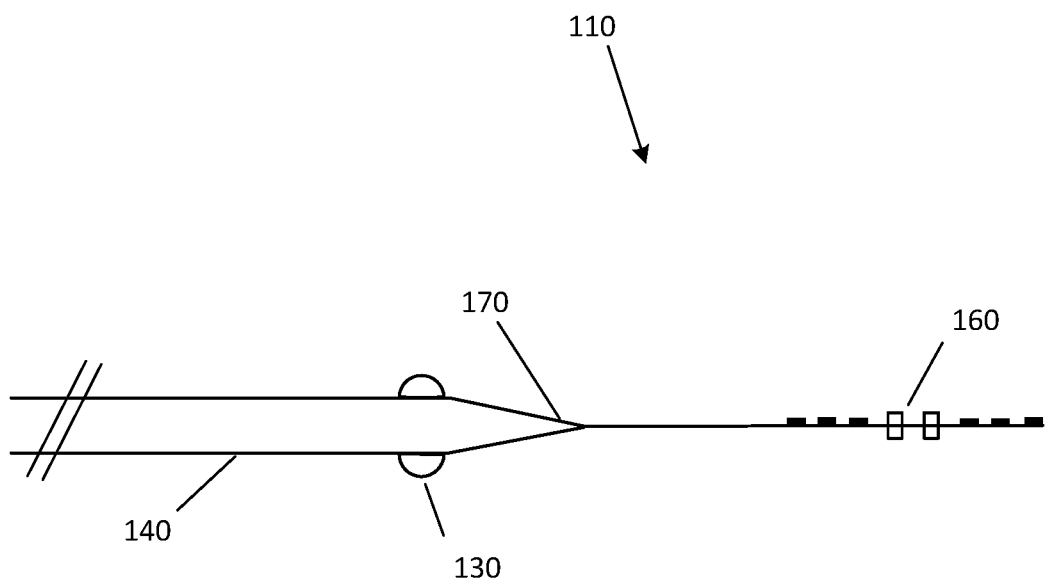
FIG. 4 is an alternate embodiment of the assembly.

In one embodiment, the assembly 110 may include a lead body 140 having at least one integrated anchor 130 and a tapered transition 170 where a distal lead 20 meets the lead body 140, and the distal lead 120 having an array of electrical contacts 160 that has a segmented contact configuration as illustrated in FIG. 4. The incorporation of contacts that are sub-segmented allows for directing of the stimulation field. The segmented electrode contacts may be placed at various positions within the entire electrode array. By way of non-limiting example, the segmented electrode contacts may be placed at first and last positions, in the center, or ⅓ of the way from each end of the array.

In another embodiment, the array of electrical contacts 260a and 260b is a bifurcated dual array with varied lengths as illustrated in FIG. 5. In this aspect, the assembly 210 may include a lead body 240 having at least one integrated anchor 230 and a tapered transition 270 where a distal lead 220 meets the lead body 240. The bifurcated dual array has two separate distal leads 220 and 222 of two differing lengths arising from a single lead body 240 and integrated anchor 230 site. The incorporation of contacts that are in a bifurcated dual array is appropriate for bilateral occipital or supraorbital nerve stimulation from a lateral entry point. One of skill in the art will appreciate that the bifurcated dual array may also be used to pass adjacent field electrodes in other body locations.

In another embodiment, the array of electrical contacts 360a and 360b is a bifurcated dual array that has two separate distal leads 320a and 320b of equal length arising from a single lead body 340 and integrated anchor 330 site as illustrated in FIG. 6. In this aspect, the assembly 300 may include a lead body 340 having at least one integrated anchor 330 and a tapered transition 370 where a distal lead 320 meets the lead body 340. The incorporation of contacts that are in a bifurcated dual array that has two separate distal leads 320a and 320b of equal length is appropriate for bilateral occipital nerve or supraorbital nerve stimulation from a midline entry point. One of skill in the art will appreciate that the bifurcated dual array that has two separate distal leads 320a and 320b of equal length may also be used to pass adjacent field electrodes in other body locations.

In another embodiment, the one or more distal leads 460 may have a paddle shape and the array of electrical contacts may have a "frond" configuration as illustrate in FIG. 7. The "frond" configuration is a small two-row array that orients electrodes so that the array of electrical contacts 460 are not perpendicular with distal lead 420. This angle allows for a larger surface area of coverage than an orthogonal paddle or cylindrical electrode would permit. In this aspect, the assembly 400 may include a lead body 440 having at least one integrated anchor 430 and a tapered transition 470 where a distal lead 420 meets the lead body 440.

In all embodiments, the electrical contacts 60 have a size that allows one or more electrical contacts 60 to fit on each of the distal leads 20. In various aspects, the array of electrical contacts 60 on each distal lead 20 may include at least 2, at least 3, at least 4, at least 5, at least 10, or at least 20 electrical contacts 60.

II. Connector

As illustrated in FIG. 1, the end of the assembly 10 that is opposite of the distal leads 20 is the connector element 50. The connector element 50 is configured to connect the assembly 10 to a power source. In a preferred embodiment, the power source is an implantable pulse generator. The implantable pulse generator may have a rechargeable battery that is recharged by an external wireless source. In another embodiment, the connector element 50 is configured to connect the assembly 10 to an implantable pulse generator that is a radio frequency receiver which is externally driven. One of skill in the art will appreciate that the connector element may be configured to receive any power sources known in the art. In preferred embodiments, the connector element 50 has an air tight hermetic seal connection to the power source.

In still another embodiment, the assembly 10 does not include a connector element and the power source for the assembly 10 is wireless. In such an embodiment, the distal leads 20 are curtailed at a terminus distal to the integrated anchors 30, wherein the widened lead body 40 incorporates dipole antennas required to receive wireless power. The wireless power source may generate an input signal with a controller module located outside of, and spaced away from, the subject's body. The input signal is then transmitted to the assembly 10 through electrical radiative coupling. The assembly 10 then converts the input signal to electrical pulses. The wireless power source transmits sufficient energy to the assembly 10 such that the assembly 10 does not require an internal power source or an internal energy storage source for operation. For examples a suitable wireless power source, see US 20140058481, which is incorporated herein by reference in its entirety.

III. Anchors

Figure 3A:
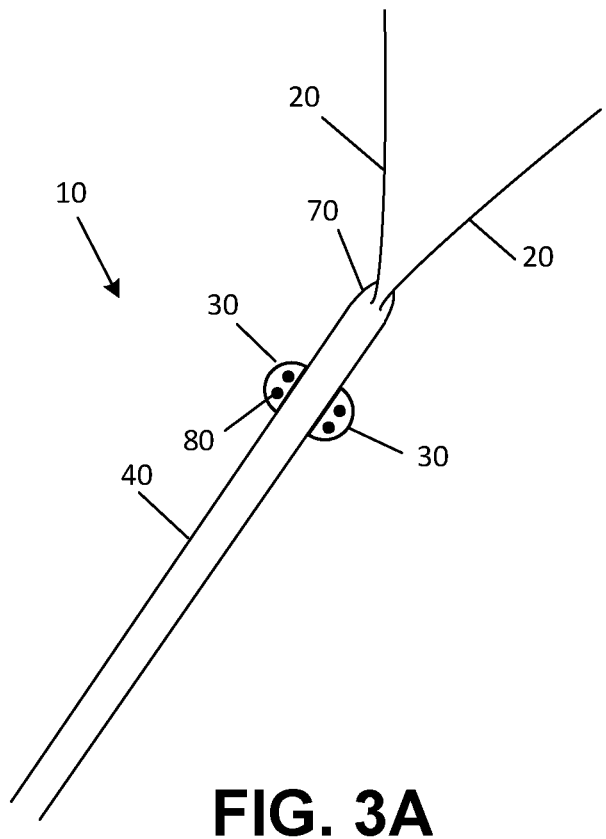
FIG. 3A is a close-up image of an embodiment of the assembly.

As illustrated in FIG. 1 and FIG. 3A, in various embodiments, the assembly has at least one integrated anchor 30. The integrated anchors 30 may be low profile and aid in reducing the migration of the assembly 10. The integrated anchors 30 may be made from a variety of materials known in the industry, preferably silicone. One of skill in the art will appreciate that the anchors may be made from any biocompatible material. The assembly 10 may include at least one, at least two, at least three, or at least four integrated anchors 30. In a preferred embodiment, the assembly 10 has two integrated anchors 30.

Figure 3B:
FIG. 3B is a cross-sectional view of the lead body with two suture-ready wing extension integrated anchors.

As illustrated in FIGS. 3A and 3B, the integrated anchors 30 are located on the lead body 40 at the tapered transition 70. In other aspects, the integrated anchors 30 may be proximal or distal to the tapered transition 70. In one aspect, the integrated anchors 30 may be butterfly anchors. Each wing of the integrated anchor 30 may have at least one aperture 80 for an anchor suture to pass. In preferred embodiments, the integrated anchors 30 have two apertures 80 for an anchor suture to pass. The integrated anchors 30 may have any number of apertures 80 for suture pass. In a non-limiting example, the integrated anchors 30 may comprise 1, 2, 3, 4, 5, 6, 7, 8, 9, or 10 apertures.

IV. Lead Body with a Tapered Transition

As illustrated in FIG. 1, the lead body 40 is between the connector element 50 and the distal leads 20. The lead body 40 is tapered at the tapered transition 70 so that the diameter of the lead body 40 near the distal leads 20 is smaller than portions of the lead body 40 that are proximate to the connector element 50. The tapered transition 70 of the lead body 40 is tapered so that the thin distal lead 20 combined with the wider lead body 40 provides flexibility while is better able to resist the stresses of high motion areas to help prevent fracture.

The diameter of the lead body 40 may range from about 2 mm to about 0.8 mm, from about 1.8 mm to about 1.5 mm, from about 1.7 mm to about 1.4 mm, from about 1.6 mm to about 1.3 mm, from about 1.5 mm to about 1.2 mm, from about 1.4 mm to about 1.1 mm, from about 1.3 mm to about 1.0 mm, from about 1.2 mm to about 0.9 mm, and from about 1.0 mm to about 0.8 mm. In preferred embodiments, the lead body 40 may be about 0.8 mm in diameter.

The tapered transition 70 of the lead body 40 may occur over a distance from about 10 to about 30 mm. The tapering of the lead body 40 may begin within about 10 mm distal of the anchor 30. The tapered transition 70 of the lead body 40 may decrease the lead body 40 diameter from about 1.0 mm to about 0.3 mm, from the proximal to distal end. In certain embodiments, the end of the tapered transition 70 of the lead body 40 may have a diameter ranging from about 1.0 mm to about 0.8 mm, from about 0.9 mm to about 0.7 mm, from about 0.8 mm to about a 0.6 mm, from about 0.7 mm to about 0.5 mm, from about 0.6 mm to about 0.4 mm, and from about 0.5 mm to about 0.3 mm. In various aspects, the tapered transition 70 may reduce the diameter of the lead body to match the diameter of the distal leads 20. One of skill in the art will appreciate that the taper dimensions may have any combination of diameters required for a specific anatomical application.

V. Peel Away Introducer

Figure 8A:
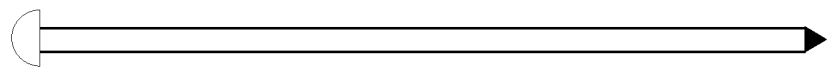
FIG. 8A is a first view of the peel-away sheath for the assembly.
Figure 8B:
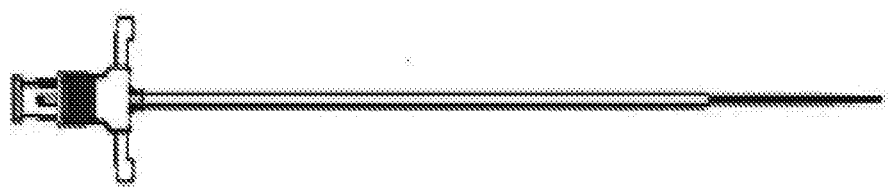
FIG. 8B is a second view of the peel-away introducer.
Figure 9:
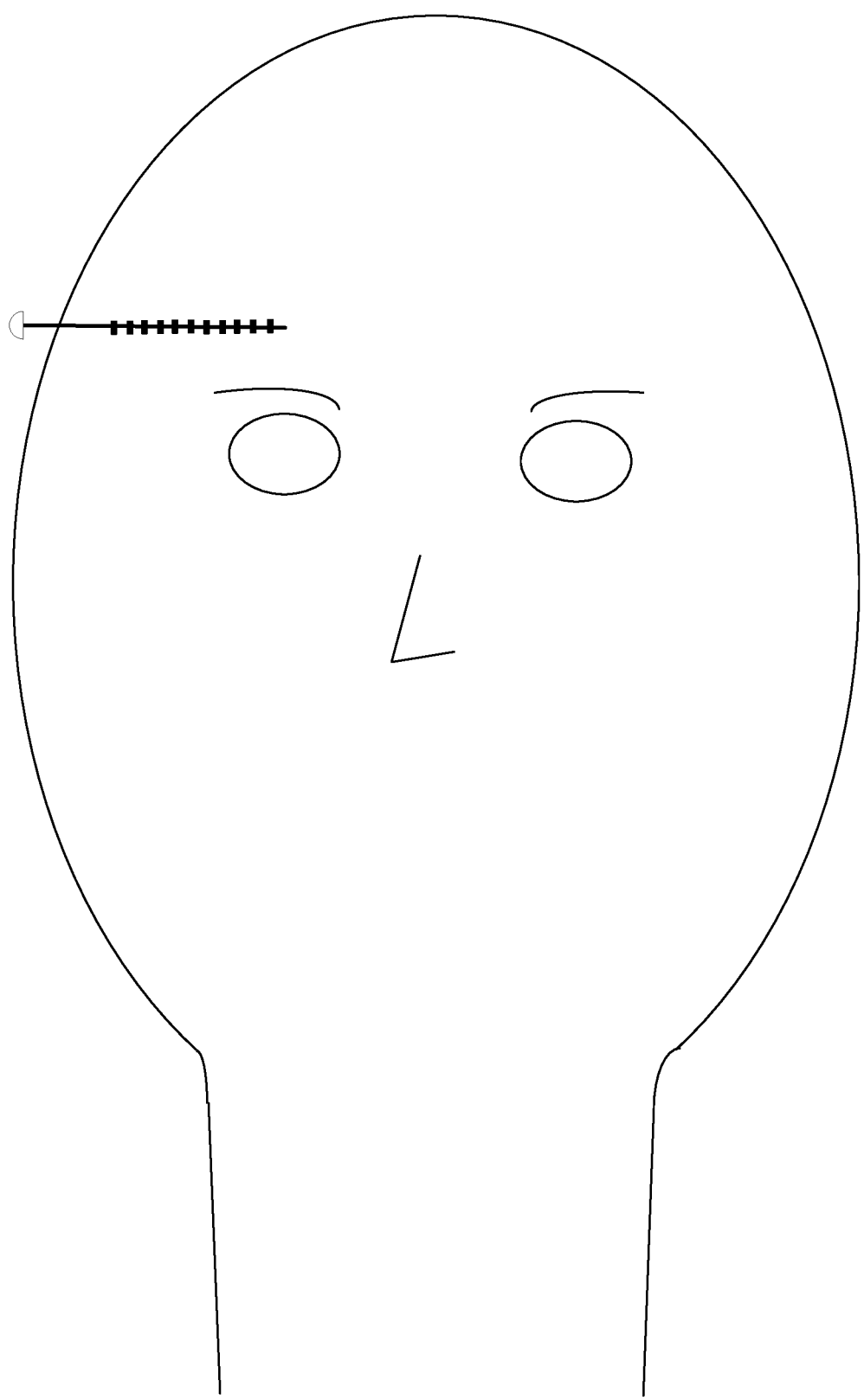
FIG. 9 is a view of the assembly implanted into the supraorbital area of a patient's face.

In some embodiments, the assembly includes a peel away introducer as illustrated in FIGS. 8A and 8B. The width of the integrated anchor 30 and of the lead body 40 is a larger diameter than the distal lead 20. Passing the entire lead assembly 10 through a tunneled hollow needle or introducer is not possible. The use of a peel-away introducer to introduce the distal lead 20 into a subcutaneous area allows for appropriate positioning. The peel-away introducer has weakened groove lines along the entire length of the sheath.

The weakened groove lines may be spaced 180 degrees from one another. These groove lines allow the sheath to be peeled away.

In embodiments where the distal lead is cylindrical, the peel away introducer has a diameter that is sufficient to accommodate the cylindrical distal lead. In an aspect, the introducer opening diameter may be about 1.5 mm. In various aspects, the diameter of the opening in the peel away introducer may range from about 1 mm to about 5 mm, from about 1 mm to about 2 mm, from about 1.5 mm to about 2.5 mm, from about 2 mm to about 3 mm, from about 2.5 mm to about 3.5 mm, from about 3 mm to about 4 mm, from about 3.5 mm to about 4.5 mm, and from about 4 mm to about 5 mm. One of skill in the art will appreciate that the opening may have any diameter required for introducing the assembly.

In embodiments where the array of electric contacts is in a frond arrangement, the distal lead may have an oval lumen. In a non-limiting example, the oval lumen may have a size of about 3.5 mm×about 1.5 mm. In various aspects, the oval opening of the lumen may range from about 2.5 mm by about 0.5 mm to about 3 mm by about 1 mm, from about 3 mm by about 1 mm to about 3.5 mm by about 1.5 mm, from about 3.5 mm by about 1.5 mm to about 4 mm by about 2 mm, from about 4 mm by about 2 mm to about 4.5 mm by about 2.5 mm, and from about 4.5 mm by about 2.5 mm to about 5 mm by about 3 mm. One of skill in the art will appreciate that the opening may have any diameter required for introducing the assembly.

VI. Method of Introducing the Assembly

A method for percutaneous placement of the assembly 10 is also disclosed. The method generally comprises: passing a hollow needle in the subcutaneous space along the course of the targeted nerve or in the targeted stimulation field; removing the inner stylet of the hollow needle and advancing a guide wire through the hollow needle; removing the hollow needle leaving the guide wire in place; threading the peel-away introducer sheath over the guide wire into position; threading the assembly 10 into position within the peel-away introducer; withdrawing the peel-away introducers sheath and peeling away for a complete removal, leaving the assembly in place; and placing sutures at the integrated anchor 30 sites to fix the assembly to the tissue at the entry point.

A hollow needle may be a hollow hypodermic needle with a very slight curve at the end. For example a hollow needle may be an epidural needle. Non-limiting examples of epidural needles include: the Crawford needle, the Tuohy needle, the Hustead needle, the Weiss needle, the Sprotte Spezial needle, the Wagner needle, the Cheng needle, the Crawley needle, the Foldes needle, the Bell needle, the Brace needle, the Lutz epidural needle, the Scott needle, the Tuohy needle with a Luer lock hub, and the Eldor. In a specific embodiment, the hollow needle is the Tuohy needle.

Placement of the assembly 10 may be used for neuromodulation of pain conditions. Accordingly, the assembly 10 may be placed in a subcutaneous location over a peripheral nerve. The assembly 10 may be used for occipital nerve stimulation (ONS) useful for the treatment of migraine and/or occipital neuralgia. Additionally, the assembly 10 may be placed near nerves of the face such as the supraorbital, infraorbital or mandibular nerves. Still further, the assembly 10 may be placed near nerves of the scalp or extremities.

Thus, an electrode for peripheral nerve stimulation and method of using has been described. It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

We claim the following:

1. An electrode assembly for peripheral nerve stimulation, the electrode comprising:
    a lead body comprising a proximal end and a distal end, wherein the distal end of the lead body comprises a tapered transition;
    at least one anchor on the lead body; and
    at least one distal lead configured to connect to the distal end of the lead body, the at least one distal lead comprising a two-row array of electrical contacts, wherein the electrical contacts are not perpendicular with the distal lead.

2. The electrode assembly of claim 1, wherein the tapered transition is at the junction of the lead body and the distal lead.

3. The electrode assembly of claim 1, wherein the tapered transition has a length of about 10 mm to about 30 mm.

4. The electrode assembly of claim 1, wherein the tapered transition has a varying diameter ranging from of about 1 mm to about 0.3 mm.

5. The electrode assembly of claim 1, wherein the at least one anchor is integrated with the lead body.

6. The electrode assembly of claim 1, wherein the at least one distal lead has a diameter of about 0.8 mm to about 0.3 mm.

7. The electrode of claim 1, wherein the at least one distal lead has a paddle shape.

8. The electrode of claim 1, wherein the array of electrical contacts has a segmented contact configuration.

9. The electrode of claim 1, wherein the array of electrical contacts is a bifurcated dual array.

10. The electrode of claim 9, wherein the electrode comprises two distal leads with varied lengths.

11. The electrode of claim 9, wherein the electrode comprises two distal leads of equal length.

12. The electrode of claim 1, wherein the power source is an implantable pulse generator.

13. The electrode of claim 1, further comprising a peel-away introducer.

14. The electrode of claim 1, further comprising a connector element for connecting to a power source.

15. The electrode of claim 1, further comprising a wireless power source.

16. An electrode for peripheral nerve stimulation the electrode comprising;
    a connector element for connecting to a power source;
    a lead body, the lead body being tapered at an end that is opposite the connector element;
    at least one anchor, wherein the one or more anchors is integrated into the lead body; and
    a distal lead comprising a two-row array of electrical contacts, wherein the electrical contacts are not perpendicular with the distal lead.

17. The electrode of claim 16, wherein the connector element is absent and the power source is wireless.

18. A method of using an electrode for peripheral nerve stimulation, the method comprising the steps of:
    (a) passing a hollow needle through an entry point and into the subcutaneous space along the course of the targeted nerve or in the targeted stimulation;

(b) removing an inner stylet of the hollow needle and advancing a guide wire in through the hollow needle;

(c) removing the hollow needle leaving the guide wire in place;

(d) threading a peel-away introducer sheath over the guide wire into position;

(e) threading the electrode assembly of claim 1 into position within the peel-away introducer;

(f) withdrawing and peeling away the peel-away introducer for a complete removal, leaving the electrode assembly in place; and (g) placing sutures at the at least one anchor to fix the electrode assembly to the tissue at the entry point.

19. The method of claim 18, wherein the hollow needle is a Tuohy needle.

* * * * *